United States Patent
Folan

(10) Patent No.: US 12,150,875 B2
(45) Date of Patent: Nov. 26, 2024

(54) STENTS WITH LINER FACILITATING STENT REMOVAL AND METHODS OF USE

(71) Applicant: Boston Scientific Scimed, Inc., Maple Grove, MN (US)

(72) Inventor: Martyn G. Folan, Loughrea (IE)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 440 days.

(21) Appl. No.: 17/474,630

(22) Filed: Sep. 14, 2021

(65) Prior Publication Data
US 2022/0087840 A1    Mar. 24, 2022

Related U.S. Application Data

(60) Provisional application No. 63/080,976, filed on Sep. 21, 2020.

(51) Int. Cl.
*A61F 2/95* (2013.01)
*A61F 2/04* (2013.01)

(52) U.S. Cl.
CPC .......... *A61F 2/95* (2013.01); *A61F 2/04* (2013.01); *A61F 2002/045* (2013.01); *A61F 2002/9528* (2013.01); *A61F 2210/0076* (2013.01)

(58) Field of Classification Search
CPC ...... A61F 2/95; A61F 2/04; A61F 2002/9528; A61F 2210/0076
See application file for complete search history.

(56) References Cited

U.S. PATENT DOCUMENTS

| | | | |
|---|---|---|---|
| 5,824,041 A | * | 10/1998 | Lenker ............... A61F 2/91 606/195 |
| 6,139,573 A | * | 10/2000 | Sogard ............... A61F 2/07 623/1.13 |
| 9,801,749 B2 | | 10/2017 | Hingston et al. |

(Continued)

OTHER PUBLICATIONS

Aiolfi et al; "Stent-in-Stent, A Safe and Effective Technique to Remove Fully Embedded Esophageal Metal Stents: Case Series and Literature Review," Endoscop Int Open 3: E296-E299, 4 pages, 2015.

(Continued)

*Primary Examiner* — Suzette J Gherbi
(74) *Attorney, Agent, or Firm* — Seager, Tufte & Wickhem, LLP

(57) ABSTRACT

An implantable treatment device configured to facilitate removal thereof after tissue ingrowth into a portion thereof, such as into an enlarged region with a diameter greater than adjacent regions. A liner is positioned within a lumen of the treatment device, with a portion spaced from the enlarged region of the treatment device. A disruption zone in the liner facilitates controlled disruption of the liner's integrity to permit a portion of a removal device inserted within the liner to extend through the liner to interact with the treatment device. The treatment device may be part of a treatment system including a removal device with an enlarged region corresponding to the treatment device enlarged region. A method of treatment involves rupturing a rupture zone in a treatment device liner to allow a portion of a removal device to extend through the liner and into engagement with a portion of the treatment device.

20 Claims, 5 Drawing Sheets

(56) References Cited

U.S. PATENT DOCUMENTS

| | | | |
|---|---|---|---|
| 10,052,220 B2* | 8/2018 | Ryan | A61F 2/04 |
| 10,682,220 B2 | 6/2020 | Folan et al. | |
| 10,779,967 B2 | 9/2020 | Walsh et al. | |
| 11,666,429 B2* | 6/2023 | Folan | A61F 2/91 |
| | | | 623/23.7 |
| 2004/0015224 A1 | 1/2004 | Armstrong et al. | |
| 2011/0093002 A1 | 4/2011 | Rucker et al. | |
| 2013/0324902 A1 | 12/2013 | Miller et al. | |
| 2018/0125630 A1* | 5/2018 | Hynes | A61F 2/0077 |
| 2018/0250118 A1* | 9/2018 | Folan | A61F 2/04 |
| 2018/0280166 A1 | 10/2018 | Walsh et al. | |
| 2018/0280167 A1* | 10/2018 | Folan | A61F 2/90 |
| 2018/0360589 A1* | 12/2018 | Nolan | A61F 2/966 |
| 2021/0015598 A1* | 1/2021 | Folan | A61F 2/0077 |

OTHER PUBLICATIONS

Davee et al; "Stent-in-Stent Technique for Removal of Embedded Partially Covered Self-Expanding Metal Stents," Surg Endosc 30-2332-2341, 10 pages, 2016.

Murino et al; "Effectiveness of Endoscopic Management Using Self-Expendable Metal Stents in a Large Cohort of Patients with Post-Bariatric Leaks," Obes Surg, 8 pages, 2015.

International Search Report and Written Opinion dated Jan. 5, 2022 for International Application No. PCT/US2021/050229.

* cited by examiner

STENTS WITH LINER FACILITATING STENT REMOVAL AND METHODS OF USE

PRIORITY

The present application is a non-provisional of, and claims the benefit of priority under 35 U.S.C. § 119 to, U.S. Provisional Application Ser. No. 63/080,976, filed Sep. 21, 2020, the disclosure of which is hereby incorporated herein by reference in its entirety for all purposes.

FIELD

The present disclosure relates to implantable medical devices and associated systems, methods of use thereof. More particularly, the present disclosure relates to removable implantable devices, associated systems for implanting and/or removing such devices, and methods of use thereof, including methods of removing a previously implanted device.

BACKGROUND

Implantable medical devices, such as radially or self-expanding stents, may be implanted in a variety of body lumens such as the esophageal tract, the gastrointestinal tract, tracheobronchial tract, urinary tract, biliary tract, vascular system, etc., and may be designed to provide a pathway for fluid flow therethrough. The compressible and flexible properties that assist in positioning may also result in migration of the device, such as due to movements of the implant site (e.g., peristalsis in the esophageal or gastrointestinal tract), and/or other characteristics of the treatment site (e.g., the generally moist and inherently lubricious environment of the esophagus, intestine, colon, etc.). One approach to reduce stent migration includes allowing a degree of tissue ingrowth therewith to promote a hyperplastic response.

However, it may become desirable to remove or reposition a partially embedded stent. A "stent-in-stent" technique may be used to remove a partially embedded stent by deploying a removal stent of equal or larger diameter within and spanning the length of the primary partially embedded treatment stent. The radial force of the secondary removal stent causes pressure necrosis of the hyperplastic tissue and allows both stents to be removed simultaneously. Typically, the removal stent is longer than the primary treatment stent, to span the regions where tissue ingrowth occurs in the primary treatment stent. A potential side effect is that secondary stenosis can occur at the protruding ends of the removal stent. Moreover, depending on various factors, such as the shape and configuration of the primary treatment stent, the liner thereof may be spaced apart from the wall of the stent. The liner typically has minimal elasticity (to prevent occlusion of the stent lumen in the event of excessive tissue ingrowth from the stent walls), and generally is considered inelastic. The liner thus retards or interferes with the expansion of the removal stent, preventing at least a portion of the removal stent from contacting the implanted treatment stent wall spaced beyond the liner. A technique other than simply puncturing the liner, which may produce variable results, possible incomplete tearing of the liner, and potential injury to tissue at the implant site, to allow the removal stent to expand as designed and to allow effective removal of both stents would be welcome.

SUMMARY

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary.

In accordance with various principles of the present disclosure, devices, systems, and methods of removing an embedded or partially embedded stent more effectively are provided.

In various embodiments described or otherwise within the scope of the present disclosure, a treatment device, having a proximal end, a distal end, and a longitudinal extent therebetween, includes a treatment device wall defining a lumen therethrough and having an interior side and an exterior side, and a liner having a liner wall extending through at least a portion of the treatment device lumen. An enlarged gap region is defined between a portion of the liner wall and the treatment device wall where the liner wall and the interior side of the treatment device wall are spaced apart more than at other regions along the longitudinal extent of the treatment device. The liner includes a disruption zone configured to facilitate disruption of the liner wall at the disruption zone. Such disruption of the liner (e.g., disruption of the integrity of the liner, such as by separation or tearing of a portion of the liner) permits a removal device placed within the liner lumen to pass the liner wall (e.g., pass through the liner wall) to interact with the treatment device wall.

In some embodiments, the liner further includes a disruptor element positioned at the disruption zone and structured to facilitate disruption of the integrity of the liner wall at the disruption zone. Optionally, the disruptor element is formed separately from the liner wall. In some embodiments, the liner wall defines a lumen therein, and the disruptor element passes through the liner wall from inside the liner lumen to outside the liner wall. Optionally, the disruptor element passes repeatedly through the liner wall about the circumference of the liner. In some embodiments, the disruptor element includes a grasping feature configured to facilitate grasping of the disruptor element to manipulate the disruptor element to disrupt the liner at the disruption zone. In some embodiments, the disruptor element includes enlarged regions configured to cause large voids in the liner wall as the disruptor element disrupts the integrity of the liner wall. In some embodiments, the enlarged regions are formed as knots in the disruptor element. In some embodiments, the enlarged regions are formed separately from the disruptor element and coupled thereto. In some embodiments, the disruptor element is a suture or wire or filament.

In some embodiments, the liner is substantially inelastic.

In some embodiments, at least a portion of the treatment device wall is configured to encourage tissue growth.

In various embodiments described or otherwise within the scope of the present disclosure, a treatment system, for a stent-in-stent removal procedure at a treatment site, includes a treatment device with a proximal end, a distal end, and a longitudinal extent therebetween, the treatment device comprising a wall defining a lumen therethrough and having an interior side and an exterior side, and a liner having a liner wall extending through at least a portion of the treatment device wall lumen and defining a liner lumen therethrough; and a removal device configured to fit within the liner lumen. The treatment device wall includes an enlarged gap region defined between a portion of the liner wall and the treatment device wall where the liner wall and the interior side of the treatment device wall are spaced apart more than at other regions along the longitudinal extent of the treatment device, and the removal device has an exterior shape configured to correspond with the shape of the interior side of the treatment device when the removal device is within the liner lumen. The liner includes a disruption zone configured to facilitate disruption of the liner wall at the disruption zone to permit the removal device, when within the liner lumen, to pass the liner wall to interact with the treatment device wall.

In some embodiments, the liner further includes a disruptor element positioned at the disruption zone and structured to facilitate disruption of the integrity of the liner wall at the disruption zone.

In some embodiments, at least a portion of the treatment device wall is configured to encourage tissue growth.

In some embodiments, the removal device is configured to interact with the treatment device to facilitate loosening of the treatment device relative to tissue at the treatment site.

In some embodiments, the removal device is radially-outwardly expandable to interact with the treatment device and to foreshorten within the treatment device such that proximal and distal ends of the removal device are positioned within the treatment device lumen and between proximal and distal ends of the treatment device.

In accordance with further aspects of the present disclosure, a method includes positioning, at a treatment site, a treatment device having a wall defining a lumen therethrough and a liner having a liner wall extending through at least a portion of the treatment device lumen and defining a liner lumen, where an enlarged gap region is defined between a portion of the liner wall and the treatment device wall where the liner wall and the treatment device wall are spaced apart more than at other regions along the longitudinal extent of the treatment device, and the liner wall is substantially inelastic and includes a disruption zone configured to facilitate disruption of the liner wall at the disruption zone. The method includes actuating the disruption zone of the liner to permit a removal device to pass through the liner wall to interact with the treatment device.

In accordance with further aspects of the present disclosure, a method includes positioning, at a treatment site, a treatment device having a wall defining a lumen therethrough and a liner having a liner wall extending through at least a portion of the treatment device lumen and defining a liner lumen, where an enlarged gap region is defined between a portion of the liner wall and the treatment device wall where the liner wall and the treatment device wall are spaced apart more than at other regions along the longitudinal extent of the treatment device, and the liner is substantially inelastic and includes a disruption zone configured to facilitate disruption of the liner wall at the disruption zone. To permit a removal device to pass through the liner wall to interact with the treatment device, the disruption zone of the liner is actuated.

In some embodiments, after actuating the disruption zone, the method further includes placing a removal device in the liner lumen, with the removal device extending through the liner to interact with the treatment device. In some embodiments, the method includes allowing the removal device to expand to interact with the treatment device and to foreshorten within the treatment device such that proximal and distal ends of the removal device are positioned within the treatment device lumen and between proximal and distal ends of the treatment device.

These and other features and advantages of the present disclosure will be readily apparent from the following detailed description, the scope of the claimed invention being set out in the appended claims.

This summary of the disclosure is given to aid understanding, and one of skill in the art will understand that each of the various aspects and features of the disclosure may advantageously be used separately in some instances, or in combination with other aspects and features of the disclosure in other instances. No limitation as to the scope of the claimed subject matter is intended by either the inclusion or non-inclusion of elements, components, or the like in this summary. Accordingly, while the disclosure is presented in terms of aspects or embodiments, it should be appreciated that individual aspects can be claimed separately or in combination with aspects and features of that embodiment or any other embodiment.

BRIEF DESCRIPTION OF THE DRAWINGS

Non-limiting embodiments of the present disclosure are described by way of example with reference to the accompanying drawings, which are schematic and not intended to be drawn to scale. The accompanying drawings are provided for purposes of illustration only, and the dimensions, positions, order, and relative sizes reflected in the figures in the drawings may vary. For example, devices may be enlarged so that detail is discernable, but is intended to be scaled down in relation to, e.g., fit within a working channel of a delivery catheter or endoscope. In the figures, identical or nearly identical or equivalent elements are typically represented by the same reference characters, and similar elements are typically designated with similar reference numbers differing in increments of 100, with redundant description is omitted. For purposes of clarity and simplicity, not every element is labeled in every figure, nor is every element of each embodiment shown where illustration is not necessary to allow those of ordinary skill in the art to understand the disclosure.

The detailed description will be better understood in conjunction with the accompanying drawings, wherein like reference characters represent like elements, as follows.

DETAILED DESCRIPTION

Figure 1:
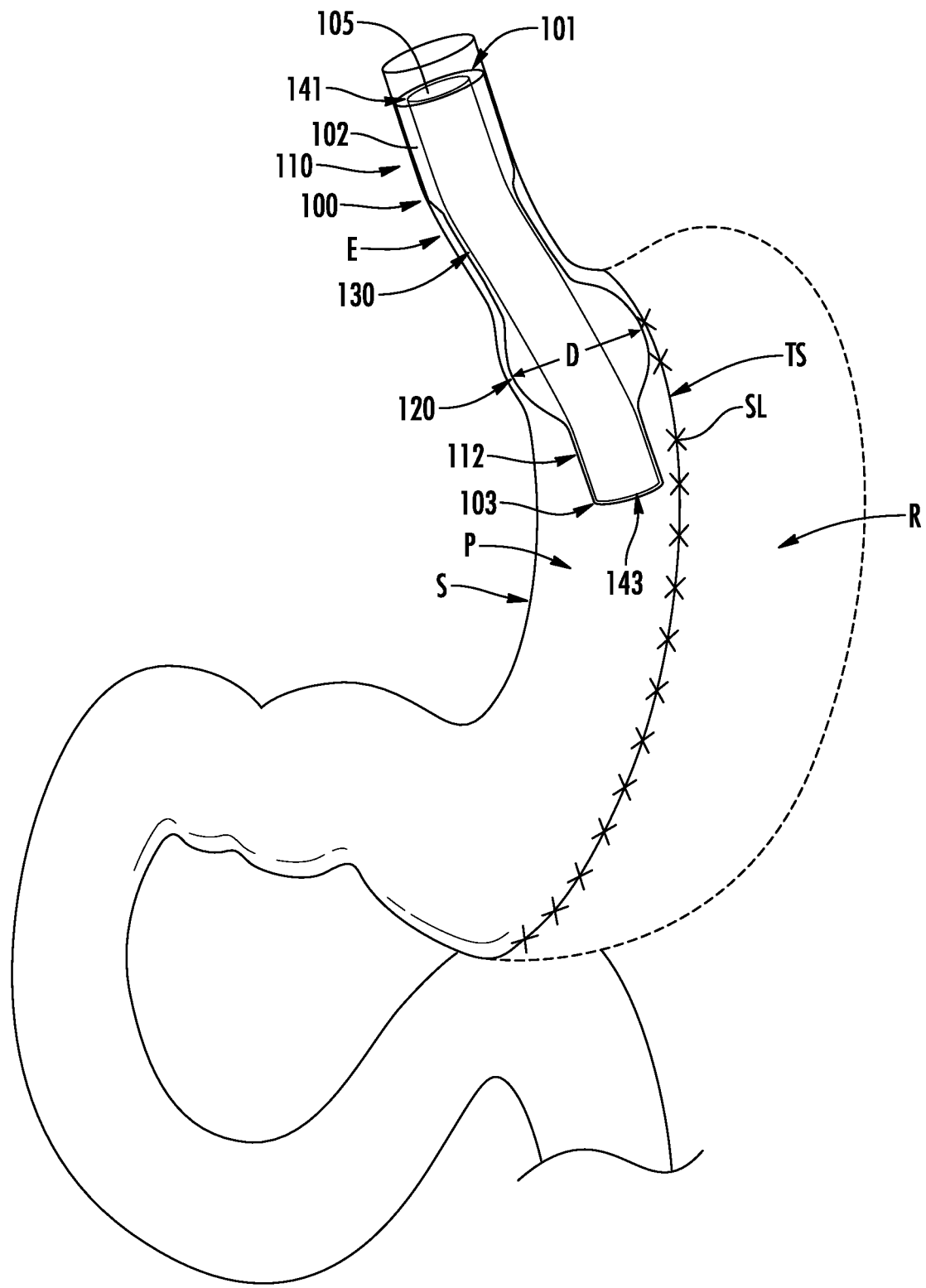
FIG. 1 is a schematic cross-sectional view of a portion of a human body with an example of a treatment device formed in accordance with various principles of the present disclosure extending therethrough.

The following detailed description should be read with reference to the drawings, which depict illustrative embodiments. It is to be understood that the disclosure is not limited to the particular embodiments described, as such may vary. All apparatuses and systems and methods discussed herein are examples of apparatuses and/or systems and/or methods implemented in accordance with one or more principles of this disclosure. Each example of an embodiment is provided by way of explanation and is not the only way to implement these principles but are merely examples. Thus, references to elements or structures or features in the drawings must be appreciated as references to examples of embodiments of the disclosure, and should not be understood as limiting the disclosure to the specific elements, structures, or features illustrated. Other examples of manners of implementing the disclosed principles will occur to a person of ordinary skill in the art upon reading this disclosure. In fact, it will be apparent to those skilled in the art that various modifications and variations can be made in the present disclosure without departing from the scope or spirit of the present subject matter. For instance, features illustrated or described as part of one embodiment can be used with another embodiment to yield a still further embodiment. Thus, it is intended that the present subject matter covers such modifications and variations as come within the scope of the appended claims and their equivalents.

It will be appreciated that the present disclosure is set forth in various levels of detail in this application. In certain instances, details that are not necessary for one of ordinary skill in the art to understand the disclosure, or that render other details difficult to perceive may have been omitted. The terminology used herein is for the purpose of describing particular embodiments only, and is not intended to be limiting beyond the scope of the appended claims. Unless defined otherwise, technical terms used herein are to be understood as commonly understood by one of ordinary skill in the art to which the disclosure belongs. All of the devices and/or methods disclosed and claimed herein can be made and executed without undue experimentation in light of the present disclosure.

As used herein, "proximal" refers to the direction or location closest to the user (medical professional or clinician or technician or operator or physician, etc., such terms being used interchangeably without intent to limit or otherwise), etc., such as when using a device (e.g., introducing the device into a patient, or during implantation, positioning, or delivery), and "distal" refers to the direction or location furthest from the user, such as when using the device (e.g., introducing the device into a patient, or during implantation, positioning, or delivery). "Longitudinal" means extending along the longer or larger dimension of an element. "Central" means at least generally bisecting a center point, and a "central axis" means, with respect to an opening, a line that at least generally bisects a center point of the opening, extending longitudinally along the length of the opening when the opening comprises, for example, a tubular element, a strut, a channel, or a bore.

In accordance with various principles of the present disclosure, an implantable treatment device has a wall defining an interior lumen, and a liner extending through the lumen. The treatment device may have a varying diameter (inner and/or outer diameter), with at least one enlarged region. The treatment device may have a treatment device wall with more than one outer diameter along the length thereof from a proximal end of the device to a distal end of the device. Of the varying diameter sizes, the inner or outer diameter (which may vary proportionately or disproportionately relative to each other along the length of the device, depending on whether the thickness of the wall of the treatment device is constant or varies) along a majority of the length of the device (either a diameter of the longest continuous extent of the device, or a diameter existing at different regions of the device with the length of such regions being the longest length of other regions with different diameters) is referenced herein as a primary or main inner or outer diameter or device body diameter of the treatment device wall. A middle region of the treatment device may be referenced herein as a saddle region for the sake of convenience and without intent to limit, and may have an outer diameter substantially the same as the primary diameter of the treatment device wall. The liner may be sized to match (e.g., to have an outer diameter slightly smaller than the inner diameter of) the primary inner diameter of the treatment device and/or the inner diameter of the saddle region. It will be appreciated that other configurations of treatment devices, such as with a treatment device wall having a substantially uniform diameter but with a liner having a variable diameter, thus defining gaps of differing sizes between the treatment device wall and the liner, are within the scope of the present disclosure. As such, at one or more extents along a treatment device to which principles of the present disclosure may be applied, the exterior side of the liner is spaced apart from the interior side of the treatment device wall to a greater extent than the spacing between the liner and other regions of the treatment device wall along the longitudinal extent of the treatment device. For the sake of simplicity, reference is made herein to an "enlarged gap region" as the region or regions of a treatment device at which a gap between a portion of the treatment device wall and the liner is greater or increased or enlarged with respect to a gap (including no gap) between the treatment device wall and the liner at other regions of the treatment device (e.g., along the longitudinal extent between the ends of the treatment device).

In accordance with one aspect of the present disclosure, the liner has a predefined disruption zone to facilitate disruption (breakage, tearing, rupturing, etc., such terms being used interchangeably herein without intent to limit) of the liner. As such, upon disruption of the liner along the disruption zone, a removal device inserted within the treatment device may be expanded beyond the liner wall to exert pressure on an interior side of the treatment device including at an enlarged gap region thereof. For instance, in one embodiment, the disruption zone is formed and positioned in a liner of substantially uniform diameter at a location adjacent an enlarged gap region of the treatment device wall. The liner of such embodiment thus may be disrupted at a location adjacent the enlarged gap region of the treatment device wall to allow a removal device to pass therethrough and into engagement with the treatment device wall.

In some embodiments, the implantable treatment device is partially coated to inhibit tissue growth. In some embodiments, the implantable treatment device is partially uncoated to facilitate tissue ingrowth. In some embodiments, the implantable treatment device may have an enlarged gap region, between a portion of the treatment device wall and the liner positioned therein, at which the treatment device wall is at least partially uncoated, promoting tissue growth at such region. The provision of a disruption zone in the liner thus may be particularly useful in allowing a removal device to extend to and to exert pressure effectively on the hyperplastic tissue to release the implantable treatment device (e.g., upon necrosis of the portion of the hyperplastic tissue ingrown into the implantable treatment device). In addition or alternatively, the provision of a disruption zone permits the removal device to expand radially and thereby foreshorten so that the proximal and distal ends of the removal device are within the treatment device (i.e., the resulting length of the removal device is shorter than the length of the treatment device). As such, tissue ingrowth into the ends of the removal device, as may occur in prior art removal devices, may be reduced or inhibited, and preferably prevented.

Reference may be made herein to an implantable device, a device, a stent, or the like, and a wall thereof may be described herein as a scaffold, such terms being understood as not intended to limit the disclosure to a specific structure not necessary for implementation of the broad principles of the present disclosure. Although the present disclosure is with reference to a stent having a particular configuration (such as an enlarged somewhat bulbous region), the principles of the present disclosure are applicable to other forms and configurations of stents or other implantable devices, including different forms and shapes of retention structures of the stent that may have varying diameter in respect of other body regions and will therefore present comparatively an enlarged gap region between a liner and larger diameter retention structures. In some embodiments, the stent may be a braided or woven stent with interstices between the filaments, sequential pattern, bounding wires, etc., forming the treatment device wall. A coating or covering for inhibiting tissue ingrowth may be provided on a portion of the implantable treatment device to reduce the force necessary to permit removal of the implanted device such as by creating a physical barrier between the tissue at the implant site and the exterior surface of the implanted device to reduce tissue ingrowth. The coating may be applied on the exterior of the implantable treatment device, and, if the implanted device is in the form of a woven or braided stent, the coating may fill the interstices in the treatment device wall. Various partially covered stents are known, such as disclosed in U.S. Pat. No. 10,682,220, titled Esophageal Stent Including An Inner Liner, and issued Jun. 16, 2020; U.S. Patent Application Publication 2018/0280166, titled Stents With Dual Tissue-Wall Anchoring Features, and published Oct. 4, 2018; and U.S. patent application Ser. No. 16/930,411, titled Stents, Systems, And Methods For Gastrointestinal Tract, and filed Jul. 16, 2020; each of which is incorporated by reference herein in its entirety for all purposes. The implantable treatment device may have bare portions (portions not covered by a covering, coating, or otherwise) to promote tissue ingrowth, such as to reduce migration of the implanted device relative to the implant site. In some instances, tissue ingrowth with or into the device wall may be desired, while passage of material through the interstices of the device wall may still not be desired. In such case, the coating may form an inner liner within the lumen or interior passage of the device, spaced inwardly from the device wall. Such liner may serve to facilitate passage of material (e.g., food, or body fluids such as for aiding digestion) through the interior passage of the device without passing through or leaking out of the wall of the device.

Some stent designs may have shapes uniquely suited for a particular treatment and/or implantation site. For instance, some stents are configured for a post bariatric surgery leak (PBSL) treatment. The body of such stent may include a knitted stent wall with a specialized body shape (e.g., with an enlarged region, such as a region including a bulb section) for interaction with the leak site/leak zone to aid in leak healing. Bariatric leaks typically occur high in the fundus region, which generally is poorly vascularized and accordingly poor in healing. The rationale around the design of a PBSL stent is that the interaction region is bare, which allows the wire forming the stent to interact with the tissue around the leak site, encouraging the tissue to develop hyperplastically and heal the leak site. A continuous central lumen through the stent is maintained across this region. A liner, such as formed from the coating material used to cover the stent to inhibit tissue ingrowth, is formed or provided within the stent lumen to isolate the leak site from any nutritional content which may pass through the stent from the esophagus to the lower stomach. An enlarged gap region, between a portion of the stent wall and the liner, may be defined along the longitudinal extent of the stent (between the ends of the stent) adjacent the enlarged region of the stent wall.

An implantable treatment device formed in accordance with principles of the present disclosure may be provided as a treatment system along with a removal device. In some embodiments, the shape (at least the exterior shape) of the removal device is configured to correspond with (substantially match or at least have common regions of corresponding variations in diameter or other shapes or geometries) the shape (at least the interior shape) of the implantable treatment device. In some embodiments, the implantable treatment device and the removal device form a stent-in-stent system facilitating removal of the implantable treatment device, if and when desired, with the removal device inserted and implanted therein.

A method of treatment utilizing an implantable treatment device having a disruption zone in accordance with principles of the present disclosure involves implanting an implantable treatment device, having a liner with a disruption zone, at a treatment site, determining if and when removal of the implantable treatment device is desired, and disrupting the disruption zone to allow expansion of a removal device inserted into the treatment device to expand beyond the liner. The removal device may be inserted into the treatment device and allowed to expand to contact the interior side of the treatment device, including the interior side of enlarged regions of the treatment device spaced apart from the liner to a greater extent than other regions of the treatment device are spaced apart from the liner before disruption of the liner. The removal device may be allowed to foreshorten within the treatment device. The removal device and the treatment device are left in place so that contact of the removal device with the interior side of the treatment device causes loosening of the treatment device (such as a result of pressure induced tissue necrosis). The treatment device and the removal device may be removed independently or simultaneously once the treatment device is sufficiently loosened, without damaging the tissue at the treatment site.

Various embodiments of a treatment device, a removal device, a treatment system, and accompanying methods of use thereof will now be described with reference to examples illustrated in the accompanying drawings. Reference in this specification to "one embodiment," "an embodiment," "some embodiments", "other embodiments", etc. indicates that one or more particular features, structures, and/or characteristics in accordance with principles of the present disclosure may be included in connection with the embodiment. However, such references do not necessarily mean that all embodiments include the particular features, structures, and/or characteristics, or that an embodiment includes all features, structures, and/or characteristics. Some embodiments may include one or more such features, structures, and/or characteristics, in various combinations thereof. Moreover, references to "one embodiment," "an embodiment," "some embodiments", "other embodiments", etc. in various places in the specification are not necessarily all referring to the same embodiment, nor are separate or alternative embodiments necessarily mutually exclusive of other embodiments. When particular features, structures, and/or characteristics are described in connection with one embodiment, it should be understood that such features, structures, and/or characteristics may also be used in connection with other embodiments whether or not explicitly described, unless clearly stated to the contrary. It should further be understood that such features, structures, and/or characteristics may be used or present singly or in various combinations with one another to create alternative embodiments which are considered part of the present disclosure, as it would be too cumbersome to describe all of the numerous possible combinations and subcombinations of features, structures, and/or characteristics. Moreover, various features, structures, and/or characteristics are described which may be exhibited by some embodiments and not by others. Similarly, various features, structures, and/or characteristics or requirements are described which may be features, structures, and/or characteristics or requirements for some embodiments but may not be features, structures, and/or characteristics or requirements for other embodiments. Therefore, the present invention is not limited to only the embodiments specifically described herein.

Turning now to the drawings, an example of a treatment device 100 formed in accordance with principles of the present disclosure is illustrated in FIG. 1 in place in a schematic representation of an example of a treatment site TS in a gastrointestinal ("GI") tract within a human body. In this non-limiting example, the treatment device 100 is a stent implanted in a portion of a GI tract which has undergone a gastric reduction procedure, such as a gastric bypass procedure, in which a portion of the stomach S has been reduced in size, such as by stapling or suturing a section of the stomach S, forming the functional stomach pouch P through which food passes (and the remnant R on the other side of the staple line SL). However, it will be appreciated that other configurations of stents or other types of treatment devices may incorporate one or more aspects of the present disclosure. The treatment device 100 illustrated in FIG. 1 has a treatment device wall 102 defining a treatment device lumen 105 therethrough through which materials, such as food, may pass through the treatment device 100. In some embodiments, the treatment device wall 102 may be considered a scaffold. The illustrated treatment device 100 has a treatment device wall 102 with regions of varying diameter (outer and/or inner diameter of the treatment device wall 102) and/or shape or configuration along the length thereof extending from a proximal end 101 of the treatment device 100 to a distal end 103 of the treatment device 100. Transitions between regions of different diameters may be sloped or otherwise shaped and/or configured to present atraumatic exterior surfaces. The diameter of the largest longitudinal extent (either continuous extent or the sum of noncontinuous regions of the treatment device 100 between the proximal end 101 and distal end 103 of the treatment device 100) of the treatment device wall 102 (e.g., the outer diameter of the treatment device wall 102) is referenced herein as the primary diameter D for the sake of convenience and without intent to limit. A first enlarged region 110 (which may be referenced alternatively as a flange without intent to limit) may be provided near the proximal end 101 of the treatment device 100 and shaped and configured to be seated in proximal region of the GI tract, such as in the esophagus E. A second enlarged region 120 (which may be referenced alternatively as a bulb without intent to limit) may be located between the proximal end 101 and the distal end 103 of the treatment device 100 and shaped and configured to be positioned to contact the stomach S wall at a treatment site TS at which a leak, perforation, or tear (or other defect in need of treatment) along the staple line SL has occurred (such site alternately referenced herein as a "leak zone"). The second enlarged region 120 may be uncoated or partially uncoated to promote tissue growth, such as hyperplasia, to promote healing of the treatment site TS. A saddle region 130 may extend between the first enlarged region 110 and the second enlarged region 120. A medial diameter section 112 may extend down further into the GI tract, in this instance, the stomach pouch P.

Figure 2:
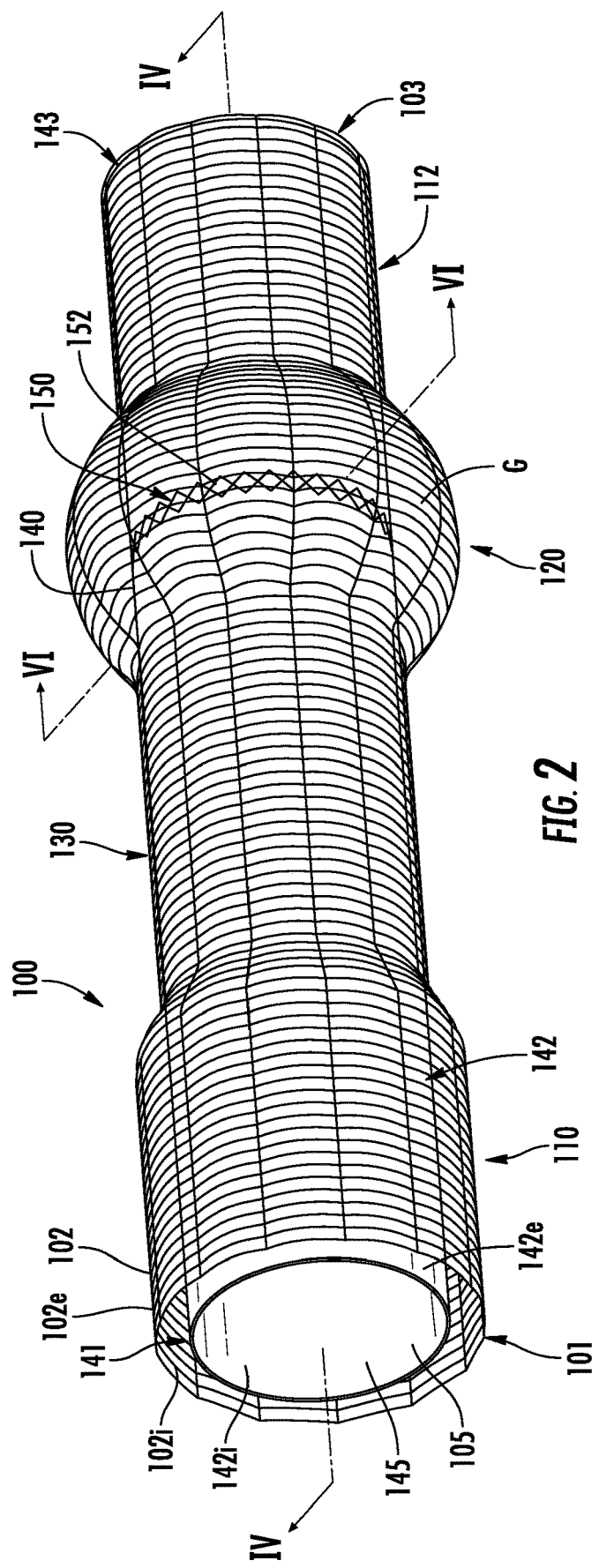
FIG. 2 is a perspective view of an example of a treatment device formed in accordance with various principles of the present disclosure.

As may be appreciated with reference to the more detailed perspective view of an example of an embodiment of a treatment device 100 illustrated in FIG. 2, a liner 140 is provided within the treatment device lumen 105. The liner 140 may extend the length of the treatment device lumen 105 from the proximal end 101 of the treatment device 100 to the distal end 103 of the treatment device 100. The liner 140 may have a liner lumen 145 extending therethrough from the proximal end 141 of the liner 140 (positioned adjacent or near the proximal end 101 of the treatment device 100) to the distal end 143 of the liner 140 (positioned adjacent or near the distal end 103 of the treatment device 100). The liner 140 may be formed and configured as known or heretofore known liners in similar implantable treatment devices, and may be substantially impervious to fluids, and may thus prevent or minimize leakage from the treatment site TS into the treatment device lumen 105. Additionally or alternatively, the liner 140 may be formed of a substantially inelastic material such that if significant tissue ingrowth occurs at the second enlarged region 120, the liner 140 inhibits or prevents excessive tissue ingrowth into the treatment device lumen 105 from occluding or stenosing the treatment device 100.

Figure 3:
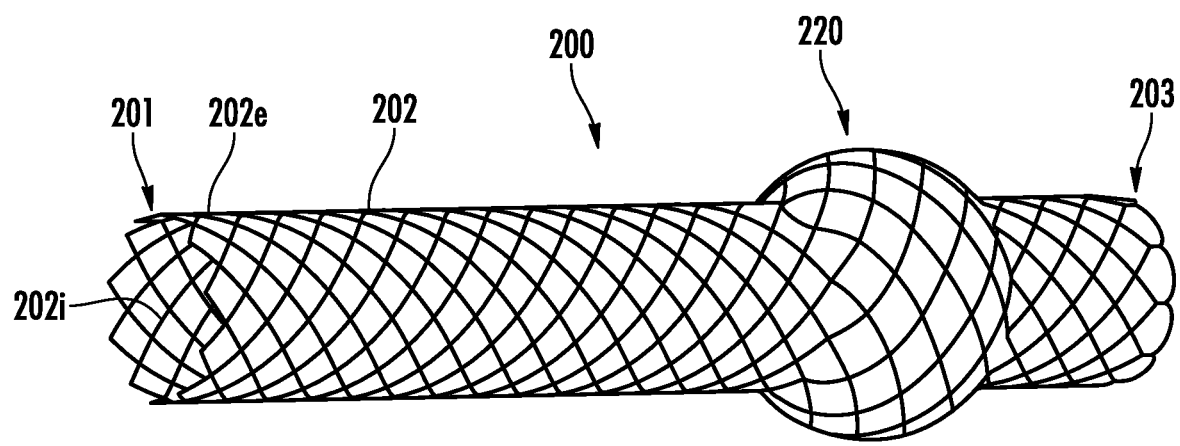
FIG. 3 a perspective view of a removal device formed in accordance with various principles of the present disclosure for use with a treatment device such as illustrated in FIG. 2.

In some instances, it may be desired to remove a treatment device 100 formed in accordance with principles of the present disclosure after a determined amount of time after implantation thereof at a treatment site TS. Removal of the treatment device 100 is envisaged to be performed, in some embodiments, with a "stent-in-stent" technique in which a removal device is implanted within the treatment device lumen 105 and exerts pressure against the interior side 102i of the treatment device wall 102 so that the exterior side 102e of the treatment device wall 102 exerts pressure on the ingrown tissue to cause loosening of the treatment device 100, such as by causing necrosis of ingrown tissue. In accordance with one embodiment, as illustrated in FIG. 3, a removal device 200 shaped and configured generally to correspond to the shape of the treatment device 100 in order to effect removal of the treatment device 100 is used. In some embodiments, at least the exterior shape of the removal device 200 is configured to correspond with the shape of the interior side 102i of the treatment device wall 102. For instance, the removal device 200 may be shaped and configured to have one or more enlarged regions corresponding to enlarged regions of a treatment device 100 (such as enlarged regions of the treatment device 100 configured, such as by being uncoated/bare, to encourage tissue growth/ingrowth) to effectively contact the treatment device 100 to apply pressure to the treatment device wall 102 to allow for ultimate removal of a partially embedded treatment device 100. In the embodiment illustrated in FIG. 3, the illustrated example of a removal device 200 has at least one enlarged removal region 220 shaped and configured to correspond to (be similar in shape and/or configuration) the second enlarged region 120 of the illustrated example of a treatment device 100, such enlarged region generally configured to be positioned at the treatment site TS. The enlarged removal region 220 is positioned relative to the proximal end 201 and the distal end 203 of the removal device 200 such that upon placement of the removal device 200 within the treatment device 100, the enlarged removal region 220 is positioned within and adjacent to the second enlarged region 120 of the treatment device 100. The removal device 200 may be expandable such that, once inserted within the treatment device 100, the removal device 200 may expand to permit contact of the enlarged removal region 220 (e.g., the exterior side 202e of the removal device wall 202) with the second enlarged region 120 (e.g., the interior side 102i of the treatment device wall 102) of the treatment device 100. The removal device 200 may be sized and/or configured to exert a sufficient amount of radially outward expansion force, such as upon expansion thereof once positioned within the treatment device 100, to exert a force (e.g., approximately 0 to 10 N) on the treatment device 100 sufficient to effect loosening of the treatment device 100 for subsequent removal from the treatment site TS. It will be appreciated that other configurations of removal devices configured to interact with other configurations of treatment devices are within the scope of the present disclosure.

Figure 5:
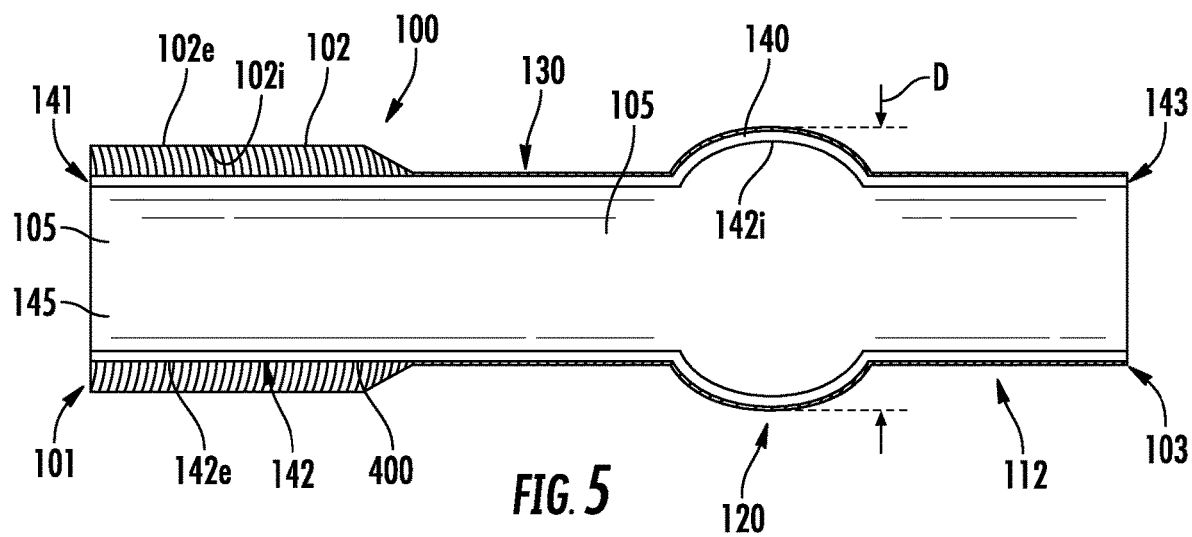
FIG. 5 is a schematic cross-sectional view of a removal device positioned within a treatment device formed in accordance with various principles of the present disclosure, showing the removal device expanding beyond the liner of the treatment device.

The removal device 200, as illustrated in FIG. 5, may be configured to be shorter than (e.g., to foreshorten upon placement) the overall length of the treatment device 100 so that, when deployed, the removal device 200 is fully contained or caged within the treatment device 100. As such, the chance of further tissue stenosis due to abrasion at the proximal and distal ends of the removal device 200 is reduced.

As described above, the liner 140 of the treatment device 100 is typically not significantly expandable and/or elastic, and therefore may retard or impede or otherwise interfere with the ability of the removal device 200 to contact the treatment device wall 102 (such as by expansion of the removal device 200) along an enlarged gap region G along the longitudinal extent of the treatment device 100(where the liner 140, particularly the exterior side 142e of the liner wall 142, may be spaced apart from the interior side 102i of the treatment device wall 102 more than at other regions along the longitudinal extent of the treatment device 100). Without sufficient expansion of the liner 140, the removal device 200 may not be able to sufficiently interact with (e.g., engage, contact, exert pressure on, etc.) the treatment device 100 (which may have bare wires for encouraging tissue growth at the leak zone and optionally within the treatment device 100), such as by extending across the gap between the liner wall 142 and the treatment device wall 102 to engage, contact, exert pressure on, etc., the interior side 102i of the treatment device wall 102, to facilitate removal the treatment device 100, such as by causing pressure necrosis of the surrounding tissue at the leak zone.

Figure 4:
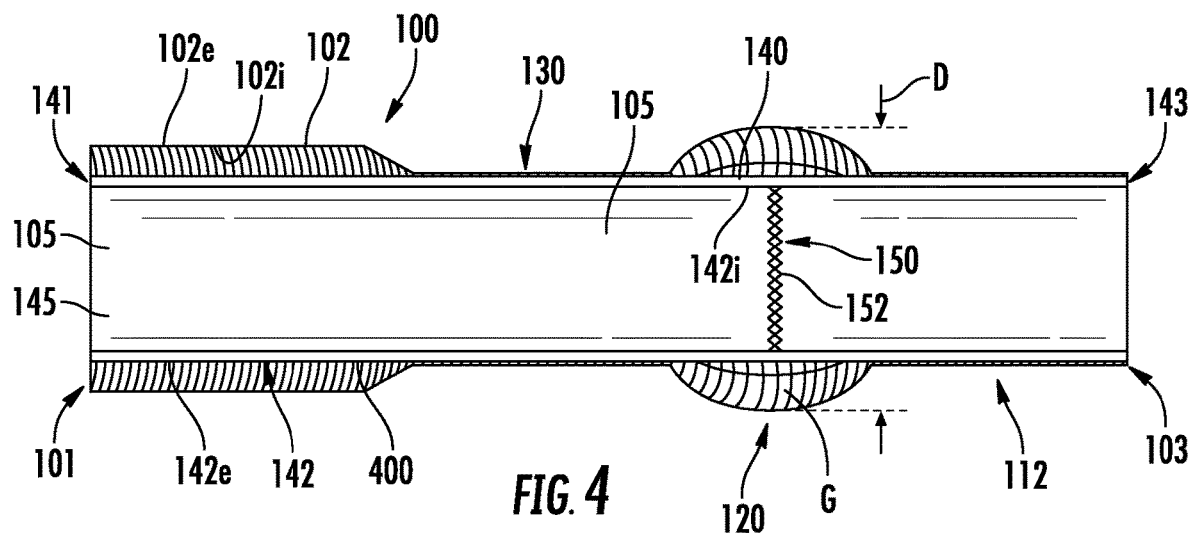
FIG. 4 is a cross-sectional view along line IV-IV of FIG. 2.

In accordance with principles of the present disclosure, the liner 140 of the embodiments illustrated in FIG. 2 and FIG. 4 is formed with a disruption zone 150. The disruption zone 150 is configured to permit a controlled manner of disrupting or breaking or tearing or rupturing of the liner 140 (such terms being used interchangeably herein, and without intent to limit, to refer to manners of altering the integrity of the structure of the liner 140 to allow the removal device 200 to extend therethrough or otherwise past the liner wall 142) to allow the removal device 200 to extend past the liner 140 to contact a region of the treatment device wall 102, such as a region of the treatment device wall 102 spaced apart from the exterior side 142e of the liner wall 142 to a greater extent or degree or amount than other regions along the longitudinal extent of the treatment device 100. In some embodiments the disruption zone 150 is positioned along the liner 140 to be located near or adjacent the leak zone region when the treatment device 100 is placed at the treatment site TS. The liner 140 may be moved (shifted, contracted axially, or otherwise) out of the way of the removal device 200, such as at the disruption zone 150, to allow expansion of the removal device 200 to interact with the treatment device 100 as desired or indicated. Although the disruption zone 150 is illustrated as positioned along an enlarged region 220 of the liner 140 corresponding to a second enlarged region 120 of the illustrated example of a treatment device 100, other locations for the disruption zone 150 allowing sufficient movement (e.g., expansion) of the removal device 200 past the liner 140 are within the scope and spirit of the present disclosure.

Figure 6:
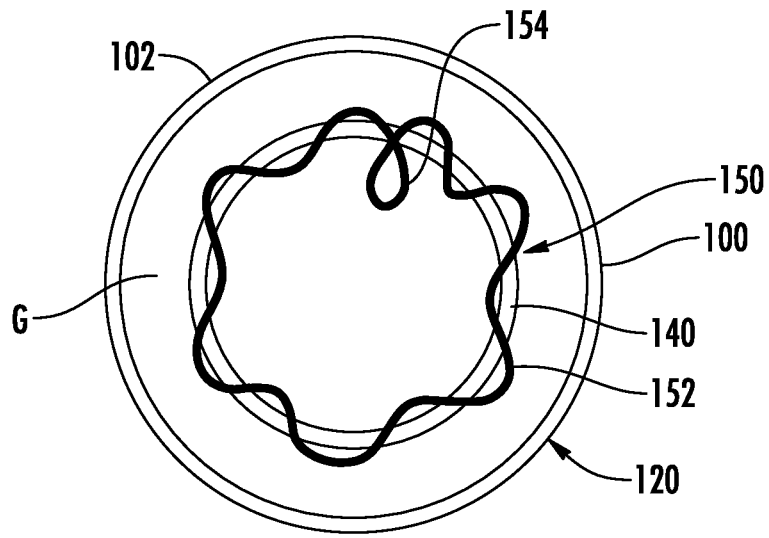
FIG. 6 is a cross-sectional view through line VI-VI of FIG. 2 of an example of a release structure formed in accordance with various principles of the present disclosure.

In one embodiment, a disruptor element 152, formed separately from the liner 140, is provided at the disruption zone 150 and structured to interact with the liner 140 at the disruption zone 150 to cause physical disruption of the liner 140, such as by manipulating the liner 140 to cause or otherwise to facilitate disruption of the liner 140 such as by disrupting the integrity of the liner wall 142. For instance, manipulation/movement of the disruptor element 152 relative to the liner 140 may disrupt the structural integrity of the liner 140. In some embodiments, radially-inward pulling of the disruptor element 152, such as from within the lumen 105 of the treatment device 100, causes the desired disruption of the liner 140. In some embodiments, the disruptor element 152 includes a suture, or filament or wire (such elements being referenced interchangeably herein without intent to limit) having a configuration at the disruption zone 150 to facilitate disruption of the disruption zone 150 upon movement of the suture relative to the disruption zone 150. In the example illustrated in FIG. 6, the disruptor element 152 may be passed or tacked from inside to outside the liner (e.g., as a continuous stitch) in a radial manner. In some embodiments, the disruptor element 152 passes repeatedly from inside to outside the liner in a radial manner around the circumference of the liner 140 at the disruption zone 150. Radially-inward pulling of the disruptor element 152, such as from within the lumen 105 of the treatment device 100, causes the disruptor element 152 to tear the liner 140 along the disruption zone 150 (optionally pursing or cinching the liner 140 radially inwards) and generally circumferentially around the liner 140 to allow the removal device 200 to be positioned within the treatment device 100 to breach and to extend past the liner 140. The removal device 200 may expand or otherwise extend towards the treatment device 100, such in the region of a leak zone, more effectively than in prior art devices, to engage the treatment device 100, as illustrated schematically in FIG. 5.

The disruptor element 152 may be removed once the liner wall 142 has been breached, or may be allowed to pass naturally through the body. In some embodiments, such as in the example illustrated in FIG. 6, the disruptor element 152 may include a grasping feature 154, such as a loop, configured to facilitate grasping of the disruptor element 152 to manipulate or actuate the disruptor element 152 to disrupt the liner 140.

Alternative embodiments of disruptor element 152 configurations are within the scope and spirit of the present disclosure. For instance, multiple disruptor elements 152, such as multiple sutures or filaments or wires, may be used. The disruptor element 152 may have patterns relative to the liner 140 that follow alternative paths or tracks or configurations (e.g., diagonal paths, longitudinal paths, etc.).

Figure 7:
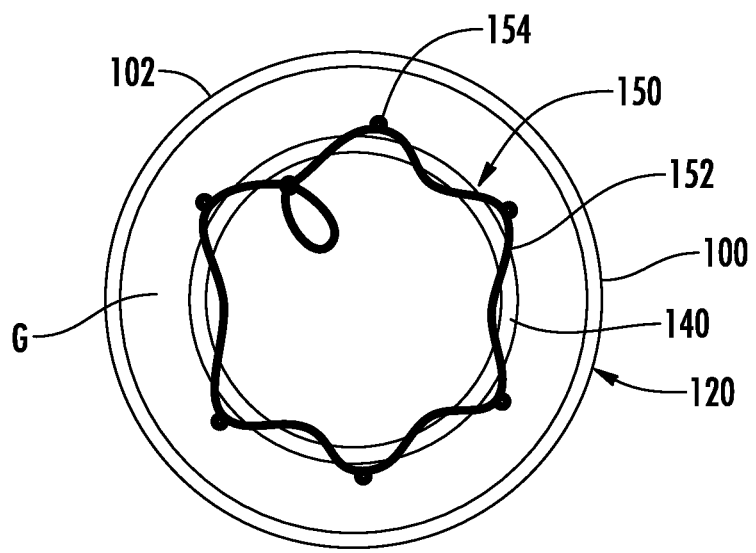
FIG. 7 is a cross-sectional of an example of a release structure formed in accordance with various principles of the present disclosure.

In some embodiments, enlarged regions may be formed on the disruptor element 152 such as along the length of the disruptor element 152. An example of an embodiment of a disruptor element 152 with enlarged regions 154 is illustrated in FIG. 7. Such enlarged regions may cause larger voids in the liner 140 as the disruptor element 152 actuates the disruption zone 150 to rupture the liner 140, and as the disruptor element 152 is retrieved, and may further facilitate rupturing of the liner 140. Such enlarged regions may be formed in a variety of manners, such as knotted sections on the outer areas of the suture line, a beading component threaded into place during manufacture, another component formed separately from the disruptor element and applied or otherwise coupled thereto (e.g., in liquid form which upon application to the disruptor element 152 solidifies, or a solid component otherwise coupled to the disruptor element 152), etc.

As may be appreciated with reference to FIG. 5, a disruption zone 150 provides several benefits over prior art treatment devices and removal devices. Removal of the liner 140 with the assistance of a disruption zone 150 in accordance with principles of the present disclosure allows radial expansion of a removal device 200 within the treatment device 100. Such radial expansion of the removal device 200 generally is accompanied by foreshortening of the removal device 200 so that the proximal end 201 and the distal end 203 of the removal device 200 are within the lumen 105 of the treatment device 100 and positioned between the proximal end 101 and the distal end 103 of the treatment device 100. As such, the potential of tissue ingrowth into the proximal end 201 and the distal end 203 of the removal device 200 (which may result in secondary stenosis in prior art removal devices) is reduced if not eliminated. Moreover, disruption of the liner 140 allows the removal device 200 to extend across an enlarged gap region G to effectively engage with the treatment device 100. The removal device 200 may thus operate effectively across the length of the treatment device 100. In embodiments in which the treatment device 100 is used to repair a leak zone by encouraging tissue ingrowth into the treatment device 100, disruption of the liner 140 allows the removal device 200 to effectively engage with substantially all regions along the length of the treatment device 100 including in the leak zone region (positioned along the leak zone), which in prior art devices has presented a challenge in view of the greater distance of the treatment device 100 from the liner 140 (and consequently the removal device, when the liner is still intact and in place) in the area of the leak zone.

Medical devices, instruments, tools, etc. which may be used in conjunction with the treatment device 100 and the removal device 200 of the present disclosure are not limited, and may include a variety of medical devices, instruments, tools, etc., for accessing body passageways, including, for example, duodenoscopes, catheters, ureteroscopes, bronchoscopes, colonoscopes, arthroscopes, cystoscopes, hysteroscopes, and the like. The treatment device 100 and the removal device 200 may be placed in accordance with known or heretofore medically-accepted procedures for the condition to be treated by the treatment device 100. The protocols for determining timing of delivery and removal may be in accordance with generally-accepted medical protocols for the condition to be treated.

A delivery device used herewith may be any suitable size, cross-sectional shape or area, and/or configuration permitting introduction and passage of medical instruments to the distal end of the delivery device. It is generally beneficial for the delivery device to be steerable, and the delivery device may have different areas of different flexibility or stiffness to promote steerability. The delivery device may include one or more working channels extending substantially longitudinally (axially) between the proximal end and the distal end of the delivery device. The delivery devices and/or overtubes associated therewith may be made from any suitable biocompatible material known to one of ordinary skill in the art and having sufficient flexibility to traverse non-straight or tortuous anatomy. Such materials include, but are not limited to, rubber, silicon, synthetic plastic, stainless steel, metal-polymer composite; metal alloys of nickel, titanium, copper cobalt, vanadium, chromium, and iron; superelastic or shape memory material such as Nitinol (nickel-titanium alloy); different layers of different materials and reinforcements. Such materials may be made of or coated with a polymeric or lubricious material to enable or facilitate passage of a deliver device therethrough. In some embodiments, the working channels may be made of or coated with a polymeric or lubricious material to facilitate passage of the introduced medical instrument(s) through the working channel(s).

The treatment device 100 may be constructed in a variety of non-limiting manners. In some embodiments, the treatment device 100 may be balloon or self-expanding. Examples of self-expanding treatment device may include stents having one or more strut members combined to form a rigid and/or semi-rigid stent structure. For example, the strut members may be formed of one or more wires or filaments which are braided, wrapped, intertwined, interwoven, weaved, knitted, looped (e.g., bobbinet-style), knotted, or the like to form a scaffold configuration. Alternatively, the treatment device 100 may be a monolithic structure formed from a cylindrical tubular member, such as a single, cylindrical tubular laser-cut tubular member (formed, for example, from Nitinol), in which the remaining portions of the tubular member form the strut members. Openings or interstices through the treatment device wall may be defined between adjacent the strut members.

The treatment device 100 may be constructed from a variety of non-limiting materials, such as, without limitation, a metal, a metal alloy, a polymer (some examples of which are disclosed below), a metal-polymer composite, ceramics, combinations thereof, and the like, or other suitable material. For example, the treatment device 100 may be constructed from a metal/metal alloy (e.g., stainless steel, such as 304V, 304L, and 316LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt—chromium-molybdenum alloys (e.g., UNS: R30035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R30003 such as ELGILOY®, PHYNOX®, and the like); platinum enriched stainless steel; titanium; combinations thereof; and the like; or any other suitable material, etc.).

In other examples, the treatment device 100 may be constructed from a polymeric material (e.g., polyethylene terephthalate (PET), poly(methyl methacrylate), polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID@ available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, biocompatible polymers, other suitable materials, or mixtures, combinations, copolymers thereof, polymer/metal composites; and the like, or other suitable polymer, etc.). In yet other examples, the treatment device 100 may be constructed from a combination of metallic and polymeric materials, such as cored or composite fibers, e.g., having a Nitinol outer shell and a platinum core. Some examples of cored or composite fibers are disclosed in U.S. Pat. Nos. 7,101,392, and 6,527,802, each of which is incorporated herein by reference in its entirety for all purposes. In still yet other examples, the treatment device 100 may include a bioabsorbable and/or biodegradable material (e.g., a poly(lactic-co-glycolic acid) polymer).

In at least some embodiments, portions or all of the devices disclosed herein, and other components of the devices described herein, may also be doped with, made of, or otherwise include a radiopaque material. Radiopaque materials are understood to be materials capable of producing a relatively bright image on a fluoroscopy screen or another imaging technique during a medical procedure. This relatively bright image aids users in determining the locations of the devices. Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the devices to achieve the same result.

In some embodiments, a degree of Magnetic Resonance Imaging (MRI) compatibility is imparted into the devices described herein. For example, devices and other components of the devices, or portions thereof, may be made of a material that does not substantially distort the image and create substantial artifacts (e.g., gaps in the image). The devices may also be made from a material that the MRI machine can image. Some materials that exhibit these characteristics include, for example, tungsten, cobalt-chromium-molybdenum alloys (e.g., UNS: R30003 such as ELGILOY®, PHYNOX®, and the like), nickel-cobalt-chromium-molybdenum alloys (e.g., UNS: R30035 such as MP35-N® and the like), nitinol, and the like, and others.

As disclosed herein, a liner 140 formed in accordance with principles of the present disclosure may be understood as a coating, where a portion of the coating is coupled to at least a portion of a stent, and a portion of the coating is spaced inwardly (e.g., floats) with respect to the treatment device wall 102. In various embodiments, the liner 140 may be a polymeric material, such as silicone, polyurethane, polyvinylidene difluoride (PVDF), Chronoflex®, or similar biocompatible polymeric formulations. In yet other embodiments, the liner 140 may include a ciliated coating (not shown) along the side 102i of the treatment device wall 102 and a region spaced inwardly of the treatment device wall 102. As shown, portions of the liner 140 may extend between strut members or filaments of the treatment device wall 102, thereby filling any spaces or interstices between adjacent strut members or filaments of the treatment device wall 102.

The foregoing discussion has broad application and has been presented for purposes of illustration and description and is not intended to limit the disclosure to the form or forms disclosed herein. It will be understood that various additions, modifications, and substitutions may be made to embodiments disclosed herein without departing from the concept, spirit, and scope of the present disclosure. In particular, it will be clear to those skilled in the art that principles of the present disclosure may be embodied in other forms, structures, arrangements, proportions, and with other elements, materials, and components, without departing from the concept, spirit, or scope, or characteristics thereof. For example, various features of the disclosure are grouped together in one or more aspects, embodiments, or configurations for the purpose of streamlining the disclosure. However, it should be understood that various features of the certain aspects, embodiments, or configurations of the disclosure may be combined in alternate aspects, embodiments, or configurations. While the disclosure is presented in terms of embodiments, it should be appreciated that the various separate features of the present subject matter need not all be present in order to achieve at least some of the desired characteristics and/or benefits of the present subject matter or such individual features. One skilled in the art will appreciate that the disclosure may be used with many modifications or modifications of structure, arrangement, proportions, materials, components, and otherwise, used in the practice of the disclosure, which are particularly adapted to specific environments and operative requirements without departing from the principles or spirit or scope of the present disclosure. For example, elements shown as integrally formed may be constructed of multiple parts or elements shown as multiple parts may be integrally formed, the operation of elements may be reversed or otherwise varied, the size or dimensions of the elements may be varied. Similarly, while operations or actions or procedures are described in a particular order, this should not be understood as requiring such particular order, or that all operations or actions or procedures are to be performed, to achieve desirable results. Additionally, other implementations are within the scope of the following claims. In some cases, the actions recited in the claims can be performed in a different order and still achieve desirable results. The presently disclosed embodiments are therefore to be considered in all respects as illustrative and not restrictive, the scope of the claimed subject matter being indicated by the appended claims, and not limited to the foregoing description or particular embodiments or arrangements described or illustrated herein. In view of the foregoing, individual features of any embodiment may be used and can be claimed separately or in combination with features of that embodiment or any other embodiment, the scope of the subject matter being indicated by the appended claims, and not limited to the foregoing description.

In the foregoing description and the following claims, the following will be appreciated. The phrases "at least one", "one or more", and "and/or", as used herein, are open-ended expressions that are both conjunctive and disjunctive in operation. The terms "a", "an", "the", "first", "second", etc., do not preclude a plurality. For example, the term "a" or "an" entity, as used herein, refers to one or more of that entity. As such, the terms "a" (or "an"), "one or more" and "at least one" can be used interchangeably herein. All directional references (e.g., proximal, distal, upper, lower, upward, downward, left, right, lateral, longitudinal, front, back, top, bottom, above, below, vertical, horizontal, radial, axial, clockwise, counterclockwise, and/or the like) are only used for identification purposes to aid the reader's understanding of the present disclosure, and/or serve to distinguish regions of the associated elements from one another, and do not limit the associated element, particularly as to the position, orientation, or use of this disclosure. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. Identification references (e.g., primary, secondary, first, second, third, fourth, etc.) are not intended to connote importance or priority, but are used to distinguish one feature from another. The following claims are hereby incorporated into this Detailed Description by this reference, with each claim standing on its own as a separate embodiment of the present disclosure. Reference signs in the claims are provided merely as a clarifying example and shall not be construed as limiting the scope of the claims in any way.

The following claims are hereby incorporated into this Detailed Description by this reference, with each claim standing on its own as a separate embodiment of the present disclosure. In the claims, the term "comprises/comprising" does not exclude the presence of other elements or steps. Additionally, although individual features may be included in different claims, these may possibly advantageously be combined, and the inclusion in different claims does not imply that a combination of features is not feasible and/or advantageous. In addition, singular references do not exclude a plurality. The terms "a", "an", "the", "first", "second", etc., do not preclude a plurality. Reference signs in the claims are provided merely as a clarifying example and shall not be construed as limiting the scope of the claims in any way.

What is claimed is:

1. A treatment device having a proximal end, a distal end, and a longitudinal extent therebetween, said treatment device comprising:
   a treatment device wall defining a lumen therethrough and having an interior side and an exterior side; and
   a liner having a liner wall extending through at least a portion of the treatment device lumen;
   wherein:
   an enlarged gap region is defined between a portion of said liner wall and said treatment device wall where said liner wall and the interior side of said treatment device wall are spaced apart more than at other regions along the longitudinal extent of said treatment device; and
   said liner includes a disruption zone configured to facilitate disruption of said liner wall by at least one of breaking, tearing, or rupturing of said liner wall.

2. The treatment device of claim 1, wherein said liner further comprises a disruptor element positioned at said disruption zone and structured to facilitate disruption of the integrity of said liner wall at said disruption zone.

3. The treatment device of claim 2, wherein said disruptor element is formed separately from said liner wall.

4. The treatment device of claim 3, wherein said liner wall defines a lumen therein, and said disruptor element passes through said liner wall from inside said liner lumen to outside said liner wall.

5. The treatment device of claim 4, wherein said disruptor element passes repeatedly through said liner wall about the circumference of said liner.

6. The treatment device of claim 3, wherein said disruptor element includes a grasping feature configured to facilitate grasping of said disruptor element to manipulate said disruptor element to disrupt said liner at the disruption zone.

7. The treatment device of claim 2, wherein said disruptor element includes enlarged regions configured to cause large voids in said liner wall as the disruptor element disrupts the integrity of said liner wall.

8. The treatment device of claim 7, wherein said enlarged regions are formed as knots in said disruptor element.

9. The treatment device of claim 7, wherein said enlarged regions are formed separately from said disruptor element and coupled thereto.

10. The treatment device of claim 2, wherein said disruptor element is a suture or wire or filament.

11. The treatment device of claim 1, wherein said liner is substantially inelastic.

12. The treatment device of claim 1, wherein at least a portion of said treatment device wall is configured to encourage tissue growth.

13. A treatment system for a stent-in-stent removal procedure at a treatment site, said system comprising:
   a treatment device with a proximal end, a distal end, and a longitudinal extent therebetween, and comprising a wall defining a lumen therethrough and having an interior side and an exterior side, and a liner having a liner wall extending through at least a portion of the treatment device wall lumen and defining a liner lumen therethrough; and
   a removal device configured to fit within the liner lumen;
   wherein:
   an enlarged gap region is defined between a portion of said liner wall and said treatment device wall where said liner wall and said interior side of said treatment device wall are spaced apart more than at other regions along the longitudinal extent of said treatment device;
   said removal device has an exterior shape configured to correspond with the shape of said interior side of said treatment device when said removal device is within the liner lumen; and said liner includes a disruption zone configured to facilitate disruption of said liner wall by at least one of breaking, tearing, or rupturing of said liner wall.

14. The treatment system of claim 13, wherein said liner further comprises a disruptor element positioned at said disruption zone and structured to facilitate disruption of the integrity of said liner wall at said disruption zone.

15. The treatment system of claim 13, wherein at least a portion of said treatment device wall is configured to encourage tissue growth.

16. The treatment system of claim 15, wherein said removal device is configured to interact with a portion of said treatment device to facilitate loosening of said treatment device relative to tissue at the treatment site.

17. The treatment system of claim 13, wherein said removal device is radially-outwardly expandable to interact with said treatment device and to foreshorten within said treatment device such that proximal and distal ends of said removal device are positioned within said treatment device lumen and between proximal and distal ends of said treatment device.

18. A method of stent-in-stent removal at a treatment site, said method comprising:
    positioning at the treatment site a treatment device having a wall defining a lumen therethrough and a liner extending through at least a portion of the treatment device lumen and defining a liner lumen, wherein an enlarged gap region is defined between a portion of the liner wall and the treatment device wall where the liner wall and the treatment device wall are spaced apart more than at other regions along the longitudinal extent of the treatment device, and the liner wall is substantially inelastic and includes a disruption zone configured to facilitate disruption of said liner wall; and
    actuating the disruption zone of the liner to disrupt the disruption zone by at least one of breaking, tearing, or rupturing the liner wall to permit a removal device to pass through the liner wall to interact with the treatment device wall.

19. The method of claim 18, further comprising, after actuating the disruption zone, placing a removal device in the liner lumen, the removal device extending through the liner to interact with the treatment device.

20. The method of claim 19, wherein the removal device is radially-outwardly expandable and placing the removal device in the liner lumen includes allowing the removal device to expand to interact with the treatment device and to foreshorten within the treatment device such that proximal and distal ends of the removal device are positioned within the treatment device lumen and between proximal and distal ends of the treatment device.

* * * * *